(12) United States Patent
Xu et al.

(10) Patent No.: US 9,932,567 B1
(45) Date of Patent: *Apr. 3, 2018

(54) MUTANT REVERSE TRANSCRIPTASE

(71) Applicant: New England Biolabs, Inc., Ipswich, MA (US)

(72) Inventors: Yan Xu, Hamilton, MA (US); Jennifer Ong, Salem, MA (US); Shengxi Guan, Stoneham, MA (US); Nicole Nichols, Reading, MA (US)

(73) Assignee: New England Biolabs, Inc., Ipswich, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/406,160

(22) Filed: Jan. 13, 2017

Related U.S. Application Data (63) Continuation of application No. 15/274,622, filed on Sep. 23, 2016, now Pat. No. 9,580,698.

(51) Int. Cl.
| | |
|---|---|
| *C12P 19/34* | (2006.01) |
| *C12N 15/10* | (2006.01) |
| *C12Q 1/686* | (2018.01) |
| *C12N 9/22* | (2006.01) |
| *C12N 9/12* | (2006.01) |
| *C12Q 1/68* | (2018.01) |

(52) U.S. Cl.
CPC .......... *C12N 9/22* (2013.01); *C12N 9/1276* (2013.01); *C12N 15/10* (2013.01); *C12P 19/34* (2013.01); *C12Q 1/686* (2013.01); *C12Y 207/07049* (2013.01); *C12Y 301/26004* (2013.01)

(58) Field of Classification Search
None
See application file for complete search history.

(56) References Cited

U.S. PATENT DOCUMENTS

| | | | |
|---|---|---|---|
| 5,017,492 A | 5/1991 | Kotewicz et al. | |
| 8,835,148 B2* | 9/2014 | Janulaitis | C12N 9/1276 435/194 |
| 9,580,698 B1* | 2/2017 | Xu | C12N 9/1276 |
| 2016/0160193 A1 | 6/2016 | Hsieh et al. | |

OTHER PUBLICATIONS

Kacian et al., 1971, Biochim. Biophys. Acta 246: 365-83.
Yang et al., 1972, Biochem. Biophys. Res. Comm. 47: 505-11.
Gerard et al., 1975, J. Virol. 15: 785-97.
Liu et al., 1977, Arch. Virol. 55 187-200.
Kato et al., 1984, J. Viral. Methods 9: 325-339.
Lueke et al., 1990, Biochern. 29: 1764-69.
Le Grice et al., 1991, J. Virol. 65: 7004-07.
Viatz et al., Nucl. Acids Res. 1999 27: 1558-1560.
Nu et al., Nat Methods. 2014 11:41-6.
Gu et al., J. Mol. Biol. 2001 305: 341-359.

(Continued)

*Primary Examiner* — Richard C Ekstrom
(74) *Attorney, Agent, or Firm* — New England Biolabs, Inc; Harriet M. Strimpel (57) ABSTRACT

A mutant MMLV reverse transcriptase that may have an improvement in one or more properties is provided. For example, the present reverse transcriptase is believed to be more efficient relative to other commercially available MMLV reverse transcriptase variants, particularly for templates with a higher GC content.

14 Claims, 3 Drawing Sheets

(56) References Cited

OTHER PUBLICATIONS

Najmudin et al, J. Mol. Biol. 296 613-632.
Das et al., Protein Sci. 2001 10: 1936-1941.
Das et al., Structure. 2004 12: 819-29.
Cote et al., Virus Res. 2008 134: 186-202.
Georgiadis et al., Structure. 1995 3: 879-92.
Crowther et al., Proteins 2004 57: 15-26.
Yasukawa et al., J. Biotechnol. 2010 150: 299-306.
Arezi et al Nucleic Acids Res. 2009 37: 473-81.
Konishi et al., Biochem. Biophys. Res. Commun. 2014 454:269-74.
Kotewicz et al., Nucleic Acids Res. 1988 16: 265-77.
Schultz et al., J. Virol. 1996 70: 8630-8638.

* cited by examiner

SEQUENCE LISTING

<160> NUMBER OF SEQ ID NOS: 2

<210> SEQ ID NO 1
<211> LENGTH: 335
<212> TYPE: PRT
<213> ORGANISM: Artificial Sequence
<220> FEATURE:
<223> OTHER INFORMATION: Synthetic construct

<400> SEQUENCE: 1

```
Thr Leu Asn Ile Glu Asp Glu Tyr Arg Leu His Glu Thr Ser Lys Glu
1               5                   10                  15

Pro Asp Val Ser Leu Gly Ser Thr Trp Leu Ser Asp Phe Pro Gln Ala
            20                  25                  30

Trp Ala Glu Thr Gly Gly Met Gly Leu Ala Val Arg Gln Ala Pro Leu
        35                  40                  45

Ile Ile Pro Leu Lys Ala Thr Ala Thr Pro Val Ser Ile Lys Gln Tyr
50                  55                  60

Pro Met Ser Gln Glu Ala Arg Leu Gly Ile Lys Pro His Ile Gln Arg
65              70                  75                  80

Leu Leu Asp Gln Gly Ile Leu Val Pro Cys Gln Ser Pro Trp Asn Thr
                85                  90                  95

Pro Leu Leu Pro Val Lys Lys Pro Gly Thr Asn Asp Tyr Arg Pro Val
            100                 105                 110

Gln Asp Leu Arg Glu Val Asn Lys Arg Val Glu Asp Ile His Pro Thr
        115                 120                 125

Val Pro Asn Pro Tyr Asn Leu Leu Ser Gly Leu Pro Pro Ser His Gln
130                 135                 140

Trp Tyr Thr Val Leu Asp Leu Lys Asp Ala Phe Phe Cys Leu Arg Leu
145                 150                 155                 160

His Pro Thr Ser Gln Pro Leu Phe Ala Phe Glu Trp Arg Asp Pro Glu
                165                 170                 175

Met Gly Ile Ser Gly Gln Leu Thr Trp Thr Arg Leu Pro Gln Gly Phe
            180                 185                 190

Lys Asn Ser Pro Thr Leu Phe Asp Glu Ala Leu His Arg Asp Leu Ala
        195                 200                 205

Asp Phe Arg Ile Gln His Pro Asp Leu Ile Leu Leu Gln Tyr Val Asp
210                 215                 220

Asp Leu Leu Leu Ala Ala Thr Ser Glu Leu Asp Cys Gln Gln Gly Thr
225                 230                 235                 240

Arg Ala Leu Leu Gln Glu Leu Gly Asp Leu Gly Tyr Arg Ala Ser Ala
                245                 250                 255

Lys Lys Ala Gln Ile Cys Gln Lys Gln Val Lys Tyr Leu Gly Tyr Leu
            260                 265                 270

Leu Lys Glu Gly Gln Arg Trp Leu Thr Glu Ala Arg Lys Glu Thr Val
        275                 280                 285

Met Gly Ile Pro Thr Pro Lys Thr Pro Arg Gln Leu Arg Glu Phe Leu
290                 295                 300

Gly Thr Ala Gly Phe Cys Arg Leu Trp Ile Pro Gly Phe Ala Glu Leu
305                 310                 315                 320

Ala Ala Pro Leu Tyr Pro Leu Thr Lys Glu Gly Thr Leu Phe Asn
                325                 330                 335
```

<210> SEQ ID NO 2
<211> LENGTH: 348
<212> TYPE: PRT

```
<213> ORGANISM: Artificial Sequence
<220> FEATURE:
<223> OTHER INFORMATION: Synthetic construct

<400> SEQUENCE: 2

Trp Gly Pro Asp Gln Gln Lys Ala Tyr Gln Glu Ile Lys Gln Ala Leu
1               5                   10                  15

Leu Thr Ala Pro Ala Leu Gly Leu Pro Asp Leu Thr Lys Pro Phe Glu
            20                  25                  30

Leu Phe Val Asp Glu Lys Gln Gly Tyr Ala Lys Gly Val Leu Thr Gln
        35                  40                  45

Lys Leu Gly Pro Trp Arg Arg Pro Val Ala Tyr Leu Ser Lys Lys Leu
    50                  55                  60

Asp Pro Val Ala Ala Gly Trp Pro Pro Cys Leu Arg Met Val Ala Ala
65                  70                  75                  80

Ile Ala Val Leu Thr Lys Asp Ala Gly Lys Leu Thr Met Gly Gln Pro
                85                  90                  95

Leu Val Ile Leu Ala Pro His Ala Val Glu Ala Leu Val Lys Gln Pro
            100                 105                 110

Pro Asp Arg Trp Leu Ser Asn Ala Arg Met Thr His Tyr Gln Ala Leu
        115                 120                 125

Leu Leu Asp Thr Asp Arg Val Gln Phe Gly Pro Val Val Ala Leu Asn
    130                 135                 140

Pro Ala Thr Leu Leu Pro Leu Pro Glu Glu Gly Leu Gln His Asn Cys
145                 150                 155                 160

Leu Asp Ile Leu Ala Glu Ala His Gly Thr Arg Pro Asp Leu Thr Asp
                165                 170                 175

Gln Pro Leu Pro Asp Ala Asp His Thr Trp Tyr Thr Asp Gly Ser Ser
            180                 185                 190

Leu Leu Gln Glu Gly Gln Arg Lys Ala Gly Ala Ala Val Thr Thr Glu
        195                 200                 205

Thr Glu Val Ile Trp Ala Lys Ala Leu Pro Ala Gly Thr Ser Ala Gln
    210                 215                 220

Arg Ala Glu Leu Ile Ala Leu Thr Gln Ala Leu Lys Met Ala Glu Gly
225                 230                 235                 240

Lys Lys Leu Asn Val Tyr Thr Asp Ser Arg Tyr Ala Phe Ala Thr Ala
                245                 250                 255

His Ile His Gly Glu Ile Tyr Arg Arg Arg Gly Leu Leu Thr Ser Glu
            260                 265                 270

Gly Lys Glu Ile Lys Asn Lys Asp Glu Ile Leu Ala Leu Leu Lys Ala
        275                 280                 285

Leu Phe Leu Pro Lys Arg Leu Ser Ile Ile His Cys Pro Gly His Gln
    290                 295                 300

Lys Gly His Ser Ala Glu Ala Arg Gly Asn Arg Met Ala Asp Gln Ala
305                 310                 315                 320

Ala Arg Lys Ala Ala Ile Thr Glu Thr Pro Asp Thr Ser Thr Leu Leu
                325                 330                 335

Ile Glu Asn Ser Ser Pro Asn Ser Arg Leu Ile Asn
            340                 345
```

MUTANT REVERSE TRANSCRIPTASE

BACKGROUND

Reverse transcriptases are multi-functional enzymes with three enzymatic activities including RNA- and DNA-dependent DNA polymerization activity, and an RNaseH activity that catalyzes the cleavage of RNA in RNA-DNA hybrids. Mutants of reverse transcriptases have disabled the RNaseH moiety to prevent unintended damage to the mRNA. These enzymes that synthesize complementary DNA (cDNA) using mRNA as a template were first identified in RNA viruses. Subsequently, reverse transcriptases were isolated and purified directly from virus particles, cells or tissues. (e.g., see Kacian et al., 1971, Biochim. Biophys. Acta 46: 365-83; Yang et al., 1972, Biochem. Biophys. Res. Comm. 47: 505-11; Gerard et al., 1975, J. Virol. 15: 785-97; Liu et al., 1977, Arch. Virol. 55 187-200; Kato et al., 1984, J. Virol. Methods 9: 325-39; Luke et al., 1990, Biochem. 29: 1764-69 and Le Grice et al., 1991, J. Virol. 65: 7004-07). More recently, mutants and fusion proteins have been created in the quest for improved properties such as thermostability, fidelity and activity.

Copying RNA can be inhibited by the presence of RNA secondary structure which can stall cDNA synthesis resulting in truncated cDNA molecules. The formation of secondary structure can be avoided at higher temperature. While this also reduces non-specific priming and thereby increases reverse transcriptase fidelity, length and yield of cDNA. However, RNA integrity can be compromised by lower enzyme activity at elevated temperatures. Further improvements are desirable to obtain optimum performance of the enzymes in library synthesis and NextGen sequencing.

SUMMARY

A mutant Moloney murine leukemia virus (MMLV) reverse transcriptase that may have an improvement in one or more properties is provided. For example, the present reverse transcriptase is believed to be more efficient relative to other commercially available MMLV reverse transcriptase variants, particularly for templates with a higher GC content. In some embodiments, use of the present MMLV reverse transcriptase may increase the proportion of full length cDNA molecules at a temperature that is higher than 42° C. (e.g., a temperature in the range of 45° C. to 60° C.). The present MMLV reverse transcriptase has at least 7 amino acid substitutions relative to the wild type MMLV reverse transcriptase.

This disclosure provides, among other things, a polypeptide comprising at least 300 contiguous amino acids of SEQ ID NO:1. The polypeptide may comprise at least amino acid residues 24-335 of SEQ ID NO:1 and, in some embodiments may have a truncated N-terminus relative to SEQ ID NO:1. In some embodiments, the polypeptide may comprise the entire contiguous sequence of SEQ ID NO:1.

In some embodiments, the polypeptide may additionally comprise an amino acid sequence that is at least 90% identical to at least 286 contiguous amino acids of SEQ ID NO:2, where the additional amino acid sequence is C-terminal to the at least 300 contiguous amino acids of SEQ ID NO:1. In some embodiments, the polypeptide may additionally comprises a purification tag and/or an exogenous sequence-specific DNA binding domain.

In some embodiments, the polypeptide may have reverse transcriptase activity. In these embodiments, the polypeptide may or may not have an RNAseH activity in addition to the reverse transcriptase activity.

In general, a method for reverse transcribing an RNA template is also provided. In some aspects, the method may comprise: (a) combining a primer, an RNA template and a reverse transcriptase comprising: i. at least 300 contiguous amino acids of SEQ ID NO:1 and optionally ii. an amino acid sequence that is at least 90% identical to at least 286 contiguous amino acids of SEQ ID NO:2 that is C-terminal to the at least 300 contiguous amino acids of SEQ ID NO:1, to produce a reaction mix and (b) incubating the reaction mix to produce cDNA copied from the RNA template.

In some aspects, the reaction mix may comprise a template switching oligonucleotide and in other aspects, the reaction mix may incubated at temperature that is higher than 42° C., e.g., at a temperature in the range of 45° C. to 65° C. The primer in the reaction mix oligo-dT primer, a random primer or a gene-specific primer, for example. As noted above, in some cases, the polypeptide may comprise an exogenous sequence-specific DNA binding domain and, may or may not have RNAseH activity.

In general, a method is provided for reverse transcribing an RNA template wherein the population of cDNA molecules produced by the method may be at least 20%, at least 40%, at least 60%, or at least 80% full length. In other aspects, the method may comprise transcribing, with increased efficiency compared with previously available reverse transcriptases, GC rich template molecules using embodiments of the reverse transcriptase described above where the template molecules may have at least 20%, 30%, 40%, 50%, 60%, 70% or 80% GC content. In embodiments, the cDNA product of the GC rich template may be at least 20%, at least 40%, at least 60%, or at least 80% full length.

These and other features of the present teachings are set forth herein.

BRIEF DESCRIPTION OF THE FIGURES

The skilled artisan will understand that the drawings, described below, are for illustration purposes only. The drawings are not intended to limit the scope of the present teachings in any way.

DETAILED DESCRIPTION OF EMBODIMENTS

Unless defined otherwise herein, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

All patents and publications, including all sequences disclosed within such patents and publications, referred to herein are expressly incorporated by reference.

Numeric ranges are inclusive of the numbers defining the range. Unless otherwise indicated, nucleic acids are written left to right in 5' to 3' orientation; amino acid sequences are written left to right in amino to carboxy orientation, respectively.

The headings provided herein are not limitations of the various aspects or embodiments of the invention. Accordingly, the terms defined immediately below are more fully defined by reference to the specification as a whole.

Unless defined otherwise, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2D ED., John Wiley and Sons, New York (1994), and Hale & Markham, THE HARPER COLLINS DICTIONARY OF BIOLOGY, Harper Perennial, N.Y. (1991) provide one of skill with the general meaning of many of the terms used herein. Still, certain terms are defined below for the sake of clarity and ease of reference.

As used herein, the term "reverse transcriptase" refers to any DNA polymerase that can copy first-strand cDNA from an RNA template. Such enzymes are commonly referred to as RNA-directed DNA polymerases and have IUBMB activity EC 2.7.7.49. In some cases, a reverse transcriptase can copy a complementary DNA strand using either single-stranded RNA or DNA as a template. MMLV reverse transcriptase is the reverse transcriptase of the Moloney murine leukemia virus.

As used herein, the term "template" refers to the substrate RNA for the reverse transcriptase to make cDNA. A template may be complex (e.g., total RNA, polyA+ RNA, mRNA, etc.) or not complex (e.g., an enriched RNA or an in vitro transcribed product).

The term "cDNA" refers to a strand of DNA copied from an RNA template. cDNA is complementary to the RNA template.

A "mutant" or "variant" protein may have one or more amino acid substitutions, deletions (including truncations) or additions (including deletions) relative to a wild-type. A variant may have less than 100% sequence identity to the amino acid sequence of a naturally occurring protein but may have any amino acid that is at least 80%, at least 85%, at least 90%, at least 95%, at least 97%, at least 98% or at least 99% identical to the amino acid sequence of the naturally occurring protein. A fusion protein is a type of protein composed of a plurality of polypeptide components that are unjoined in their naturally occurring state. Fusion proteins may be a combination of two, three or even four or more different proteins. The term polypeptide includes fusion proteins, including, but not limited to, a fusion of two or more heterologous amino acid sequences, a fusion of a polypeptide with: a heterologous targeting sequence, a linker, an immunologically tag, a detectable fusion partner, such as a fluorescent protein, β-galactosidase, luciferase, etc., and the like. A fusion protein may have one or more heterologous domains added to the N-terminus, C-terminus, and or the middle portion of the protein. If two parts of a fusion protein are "heterologous", they are not part of the same protein in its natural state.

The term "non-naturally occurring" refers to a composition that does not exist in nature. Variant proteins are non-naturally occurring. In some embodiments, "non-naturally occurring" refers to a protein that has an amino acid sequence and/or a post-translational modification pattern that is different to the protein in its natural state. A non-naturally occurring protein may have one or more amino acid substitutions, deletions or insertions at the N-terminus, the C-terminus and/or between the N- and C-termini of the protein. A "non-naturally occurring" protein may have an amino acid sequence that is different to a naturally occurring amino acid sequence (i.e., having less than 100% sequence identity to the amino acid sequence of a naturally occurring protein) but that that is at least 80%, at least 85%, at least 90%, at least 95%, at least 97%, at least 98% or at least 99% identical to the naturally occurring amino acid sequence. In certain cases, a non-naturally occurring protein may contain an N-terminal methionine or may lack one or more post-translational modifications (e.g., glycosylation, phosphorylation, etc.) if it is produced by a different (e.g., bacterial) cell.

In the context of a nucleic acid, the term "non-naturally occurring" refers to a nucleic acid that contains: a) a sequence of nucleotides that is different to a nucleic acid in its natural state (i.e. having less than 100% sequence identity to a naturally occurring nucleic acid sequence), b) one or more non-naturally occurring nucleotide monomers (which may result in a non-natural backbone or sugar that is not G, A, T or C) and/or c) may contain one or more other modifications (e.g., an added label or other moiety) to the 5'-end, the 3' end, and/or between the 5'- and 3'-ends of the nucleic acid.

In the context of a preparation, the term "non-naturally occurring" refers to: a) a combination of components that are not combined by nature, e.g., because they are at different locations, in different cells or different cell compartments; b) a combination of components that have relative concentrations that are not found in nature; c) a combination that lacks something that is usually associated with one of the components in nature; d) a combination that is in a form that is not found in nature, e.g., dried, freeze dried, crystalline, aqueous; and/or e) a combination that contains a component that is not found in nature. For example, a preparation may contain a "non-naturally occurring" buffering agent (e.g., Tris, HEPES, TAPS, MOPS, tricine or MES), a detergent, a dye, a reaction enhancer or inhibitor, an oxidizing agent, a reducing agent, a solvent or a preservative that is not found in nature.

Figure 1:
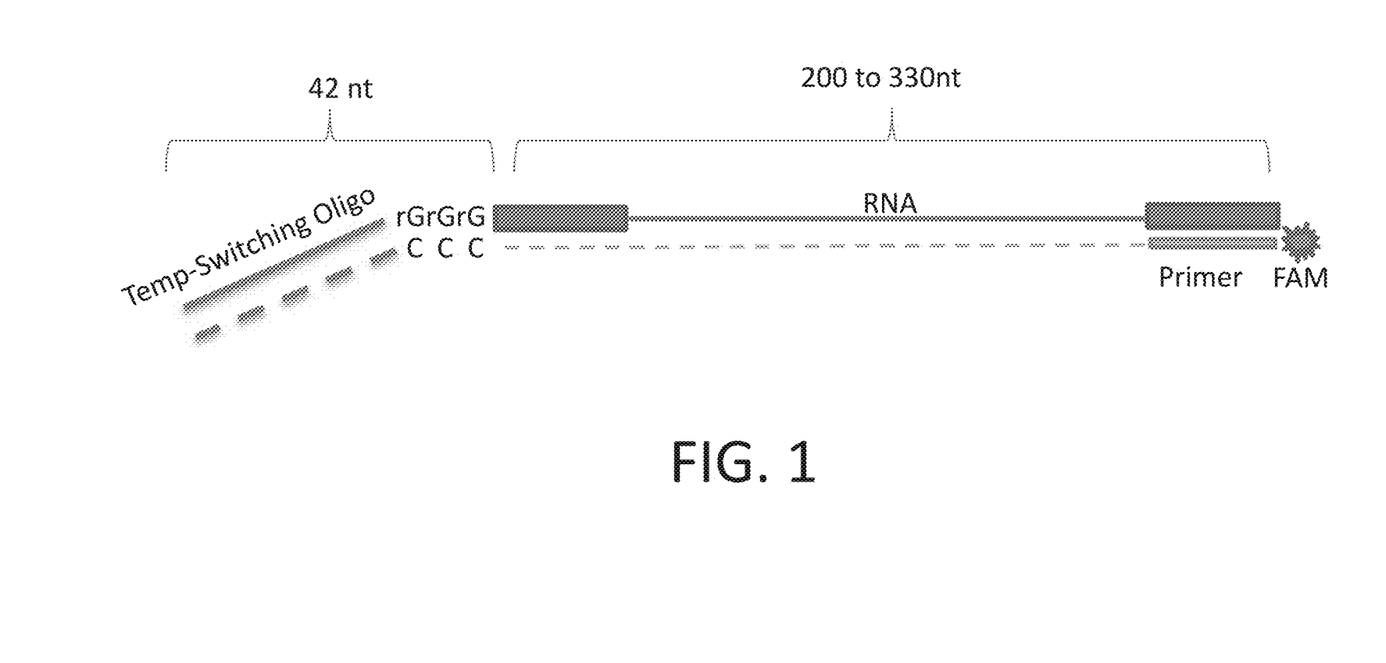
FIG. 1 shows some of the components used in the template switching assay described in the Examples section.

The term "template-switching" refers to a reverse transcription reaction in which the reverse transcriptase switches template from an RNA molecule to a synthetic oligonucleotide (which usually contains two or three Gs at its 3' end, thereby copying the sequence of the synthetic oligonucleotide onto the end of the cDNA. Template switching is generally described in Matz et al., Nucl. Acids Res. 1999 27: 1558-1560 and Wu et al., Nat Methods. 2014 11: 41-6. In template switching (and as illustrated in FIG. 1) a primer hybridizes to a RNA molecule. This primer serves as a primer for a reverse transcriptase that copies the RNA molecule to form a complementary cDNA molecule. In copying the RNA molecule, the reverse transcriptase commonly travels beyond the 5' end of the mRNA to add non-template nucleotides to the 3' end of the cDNA (typically Cs). Addition of an oligonucleotide that has ribonucleotides or deoxyribonucleotides that are complementary to the non-template nucleotides added onto the cDNA (e.g., a "template switching" oligonucleotide that typically has two or three Gs at its 3' end), the reverse transcriptase will jump templates from the RNA template to the oligonucleotide template, thereby producing a cDNA molecule that has the complement of the template switching oligonucleotide at it's 3' end.

The term "RNAseH activity" refers to an activity that hydrolyzes the RNA in RNA/DNA hybrid. Many reverse transcriptases have an RNAseH activity that can be inactivated by truncation or by substitution.

The term "primer" refers to an oligonucleotide that is capable, upon forming a duplex with a polynucleotide template, of acting as a point of initiation of nucleic acid synthesis and being extended from its 3' end along the template so that an extended duplex is formed. The sequence of nucleotides added during the extension process is determined by the sequence of the template polynucleotide. Primers are of a length compatible with their use in synthesis of primer extension products, and can are in the range of between 8 to 100 nucleotides in length, such as 10 to 75, 15 to 60, 15 to 40, 18 to 30, 20 to 40, 21 to 50, 22 to 45, 25 to 40, and so on, more typically in the range of between 18 to 40, 20 to 35, 21 to 30 nucleotides long, and any length between the stated ranges. Primers are usually single-stranded. Primers have a 3' hydroxyl.

The term "primer extension" as used herein refers to both to the synthesis of DNA resulting from the polymerization of individual nucleoside triphosphates using a primer as a point of initiation, and to the joining of additional oligonucleotides to the primer to extend the primer. Primers can incorporate additional features which allow for the detection or immobilization of the primer but do not alter the basic property of the primer, that of acting as a point of initiation of DNA synthesis. For example, primers may contain an additional nucleic acid sequence at the 5' end which does not hybridize to the target nucleic acid, but which facilitates cloning of the amplified product. The region of the primer which is sufficiently complementary to the template to hybridize is referred to herein as the hybridizing region. The terms "target region" and "target nucleic acid" refers to a region or subsequence of a nucleic acid which is to be reverse transcribed.

A polypeptide comprising at least 300 contiguous amino acids of SEQ ID NO:1 is provided. The first 23 amino acids can be removed from MMLV reverse transcriptase without altering the polymerase activity of that enzyme (see, e.g., Gu et al., J. Mol. Biol. 305: 341-359, Najmudin et al, J. Mol. Biol. 296 613-632 and Das et al., Protein Sci. 2001 10: 1936-1941). As such, some embodiments, the polypeptide may have a truncated N-terminus relative to SEQ ID NO:1. In some embodiments, the polypeptide may comprises amino acid residues 24-335 of SEQ ID NO:1, e.g., the entire contiguous sequence of SEQ ID NO:1. The present polypeptide may contain 5, 6, or 7 or more amino acid substitutions relative to the corresponding sequence in the wild type MMLV reverse transcriptase.

The polypeptide may additionally comprise an amino acid sequence that is at least 90% (e.g., at least 95%, at least 98%, at least 99% or at least 100%) identical to at least 286 contiguous amino acids (e.g., at least 300 contiguous amino acids, at least 325 contiguous amino acids or at least 336 contiguous amino acids) of SEQ ID NO:2, where SEQ ID NO:2 is the sequence of the C-terminal part of an MMLV reverse transcriptase, shown below:

WGPDQQKAYQEIKQALLTAPALGLPDLTKP-FELFVDEKQGYAKGVLTQKLGPWRRPVAYLSK-KLDP VAAGWPPCLRMVAAIAVLTKDAGKLT-MGQPLVILAPHAVEALVKQPPDRWLSNARMTH-YQALLL DTDRVQFGPVVALNPATLL-PLPEEGLQHNCLDILAEAHGTRPDLTDQPLP-DADHTWYTDGSSLLQE GQRKAGAAVTTETEVI-WAKALPAGTSAQRAELIALTQALKMAEGKKL-NVYTDSRYAFATAHIHGEIY RRRGLLTSEG-KEIKNKDEILALLKALFLPKRLSIIHCPGHQKGH-SAEARGNRMADQAARKAAITETPDT STLLIENS-SPNSRLIN (SEQ ID NO:2)

This additional sequence may be positioned C-terminal to the at least 300 contiguous amino acids of SEQ ID NO: 1. It is known that as many as 62 residues can be removed from the C-terminus of the MMLV reverse transcriptase (see, e.g., U.S. Pat. No. 5,017,492) without significantly altering the polymerase activity. As such, in some embodiments, the additional amino acid sequence may lack the C-terminal 3, 5, 10, 12, 15, 30, 50 or 62 amino acids of SEQ ID NO:2.

The MMLV reverse transcriptase has been crystallized (see, e.g., Das et al., Structure. 2004 12: 819-29), the structure-functional relationships in MMLV reverse transcriptase have been studied (see, e.g., Cote et al., Virus Res. 2008 134: 186-202, Georgiadis et al., Structure. 1995 3: 879-92 and Crowther et al., Proteins 2004 57: 15-26) and many mutations in MMLV reverse transcriptase are known (see, e.g., Yasukawa et al., J. Biotechnol. 2010 150: 299-306, Arezi et al Nucleic Acids Res. 2009 37: 473-81 and Konishi et al., Biochem. Biophys. Res. Commun. 2014 454:269-74, among many others). It is also known that one can truncate the MMLV reverse transcriptase from either ends, and add exogenous sequences to either end (see, e.g., U.S. Pat. No. 5,017,492), without abolishing activity. As such, MMLV reverse transcriptase variants are well known.

In some embodiments, the polypeptide may additionally comprises an exogenous domain and/or a purification tag (e.g., a His tag or the like) at either terminus. In some embodiments, the polypeptide may comprise a sequence-specific DNA binding protein domain, which domain has been shown to increase the processivity of other polymerases (see, e.g., US 2016/0160193). In some embodiments the sequence-specific DNA binding protein domain may be a DNA binding protein domain listed in the following table (as found in US 2016/0160193).

| DNA-binding protein Tfx | BD-51 | gi|499321160 |
| AbrB/MazE/MraZ-like | BD-52 | gi|499321199 |
| "Winged helix" DNA-binding domain | BD-54 | gi|499322061 |
| Ribbon-helix-helix protein, copG family | BD-62 | gi|499321149 |
| lambda repressor-like | BD-63 | gi|499322443 |
| DNA-binding domains Resolvase-like | BD-67 | gi|499322676 |
| "Winged helix" DNA-binding domain | BD-71 | gi|499322676 |
| "Winged helix" DNA-binding domain | BD-74 | gi|499322255 |
| "Winged helix" DNA-binding domain | BD-75 | gi|499322388 |
| "Winged helix" DNA-binding domain | BD-81 | gi|499322131 |
| "Winged helix" DNA-binding domain | BD-82 | gi|499321342 |
| "Winged helix" DNA-binding domain | BD-85 | gi|499321130 |
| "Winged helix" DNA-binding domain | BD-86 | gi|499322705 |
| "Winged helix" DNA-binding domain | BD-88 | gi|499320855 |
| "Winged helix" DNA-binding domain | BD-89 | gi|499322250 |
| "Winged helix" DNA-binding domain | BD-91 | gi|499321633 |
| "Winged helix" DNA-binding domain | BD-92 | gi|490170077 |
| "Winged helix" DNA-binding domain | BD-93 | gi|499321272 |
| "Winged helix" DNA-binding domain | BD-94 | gi|499320919 |
| "Winged helix" DNA-binding domain | BD-97 | gi|499320853 |
| "Winged helix" DNA-binding domain | BD-98 | gi|499321734 |
| "Winged helix" DNA-binding domain | BD-100 | gi|499322439 |
| "Winged helix" DNA-binding domain | BD-102 | gi|499322707 |
| "Winged helix" DNA-binding domain | BD-109 | gi|499321112 |
| HCP-like | BD-02 | gi|351675391 |
| Helix-turn-helix domain, rpiR family | BD-03 | gi|500479591 |
| Helix-turn-helix domain, rpiR family | BD-04 | gi|15643984 |
| Bacterial regulatory proteins, lacI family | BD-07 | gi|15643711 |

-continued

| | | |
|---|---|---|
| Bacterial regulatory proteins, lacI family | BD-08 | gi\|15643974 |
| Bacterial regulatory proteins, lacI family | BD-09 | gi\|15643956 |
| Bacterial regulatory proteins, lacI family | BD-11 | gi\|500480095 |
| lambda repressor-like DNA-binding domains | BD-12 | gi\|15643421 |
| "Winged helix" DNA-binding domain | BD-14 | gi\|15644350 |
| "Winged helix" DNA-binding domain | BD-16 | gi\|24159093 |
| "Winged helix" DNA-binding domain | BD-18 | gi\|15643139 |
| "Winged helix" DNA-binding domain | BD-23 | gi\|15642807 |
| "Winged helix" DNA-binding domain | BD-24 | gi\|15643159 |
| "Winged helix" DNA-binding domain | BD-30 | gi\|15643333 |
| "Winged helix" DNA-binding domain | BD-32 | gi\|15643055 |
| "Winged helix" DNA-binding domain | BD-37 | gi\|15643827 |
| "Winged helix" DNA-binding domain | BD-43 | gi\|15643699 |
| Homeodomain-like | BD-45 | gi\|15643788 |

In some embodiments, the polypeptide may have reverse transcriptase activity. In these embodiments, the polypeptide may or may not have an RNAseH activity in addition to the reverse transcriptase activity. Examples of MMLV reverse transcriptase that lack the RNAseH activity are known (see, e.g., Kotewicz et al., Nucleic Acids Res. 1988 16: 265-77 and Schultz et al., J. Virol. 1996 70: 8630-8).

A method for reverse transcribing an RNA template is also provided. In some embodiments, this method may comprise: (a) combining a primer, an RNA template, a reverse transcriptase comprising: i. at least 300 contiguous amino acids of SEQ ID NO:1, as described above, and ii. an amino acid sequence that is at least 90% identical to at least 286 contiguous amino acids of SEQ ID NO:2 (as described above) that is C-terminal to the at least 300 contiguous amino acids of SEQ ID NO:1, as well as any other components that may be necessary or desirable to perform a reverse transcription (e.g., salt, nucleotides, RNAse inhibitor, buffer, etc.), to produce a reaction mix; and (b) incubating the reaction mix to produce cDNA copied from the RNA template. The RNA template may be any type of RNA template, e.g., total RNA, polyA$^+$ RNA, capped RNA, enriched RNA etc., and the RNA can be from any source, e.g., bacteria, mammals, an in vitro transcription reaction, etc., methods for the making of which are known. The RNA template may contain RNA molecules that are at least 1 kb in length, e.g., at least 2 kb, at least 3 kb or at least 5 kb and, in some embodiments, at least some of the molecules in the RNA template may have a GC content of at least 50%, at least 60%, at least 70%, or at least 80%. The primer in the reaction mix may be any type of primer, e.g., an oligo-dT primer, a random primer or a gene-specific primer, for example, which primers are commonly used to make cDNA. In some embodiments, the reaction mix may comprise a template switching oligonucleotide, as described above.

In some embodiments, the reaction mix may be incubated at temperature that is higher than 42° C., e.g., at a temperature in the range of 45° C. to 60° C. In some embodiments, the reaction mix may be incubated at a temperature in the range of 42° C. to 45° C., 48° C. to 51° C., 51° C. to 54° C., 54° C. to 57° C., 57° C. to 60° C. or 60° C. to 65° C. In some embodiments, the population of cDNA molecules produced by the method may be at least 20%, at least 40%, at least 60%, or at least 80% full length. The polymerase can reverse transcribe GC rich template molecules with increased efficiency compared with previously available reverse transcriptases where the template molecules may have at least 20%, 30%, 40%, 50%, 60%, 70% or 80% GC content (see for example, FIG. 3).

If an oligo-dT or a random primer is used in the method, then the may be used to make a cDNA library that can be sequenced or used for gene expression analysis. Alternatively, if a gene-specific primer is used, then method may be used for RT-PCR (e.g., quantitative RT-PCR) and other similar analyses.

All references cited herein are incorporated by reference.

EXAMPLES

Aspects of the present teachings can be further understood in light of the following examples, which should not be construed as limiting the scope of the present teachings in any way.

Superscript IV, Protoscript II and a variant MMLV reverse transcriptase referred to as "M19H" were tested in a template switching assay to determine the efficiency of reverse transcription of templates that have different GC contents (14% to 88.6%). The M19H mutant comprises the following N-terminal sequence:

```
                                        (SEQ ID NO: 1)
TLNIEDEYRLHETSKEPDVSLGSTWLSDFPQAWAETGGMGLAVRQAPLIIP

LKATATPVSIKQYPMSQEARLGIKPHIQRLLDQGILVPCQSPWNTPLLPVK

KPGTNDYRPVQDLREVNKRVEDIHPTVPNPYNLLSGLPPSHQWYTVLDLKD

AFFCLRLHPTSQPLFAFEWRDPEMGISGQLTWTRLPQGFKNSPTLFDEALH

RDLADFRIQHPDLILLQYVDDLLLAATSELDCQQGTRALLQELGDLGYRAS

AKKAQICQKQVKYLGYLLKEGQRWLTEARKETVMGIPTPKTPRQLREFLGT

AGFCRLWIPGFAELAAPLYPLTKEGTLFN
```

Figure 2:
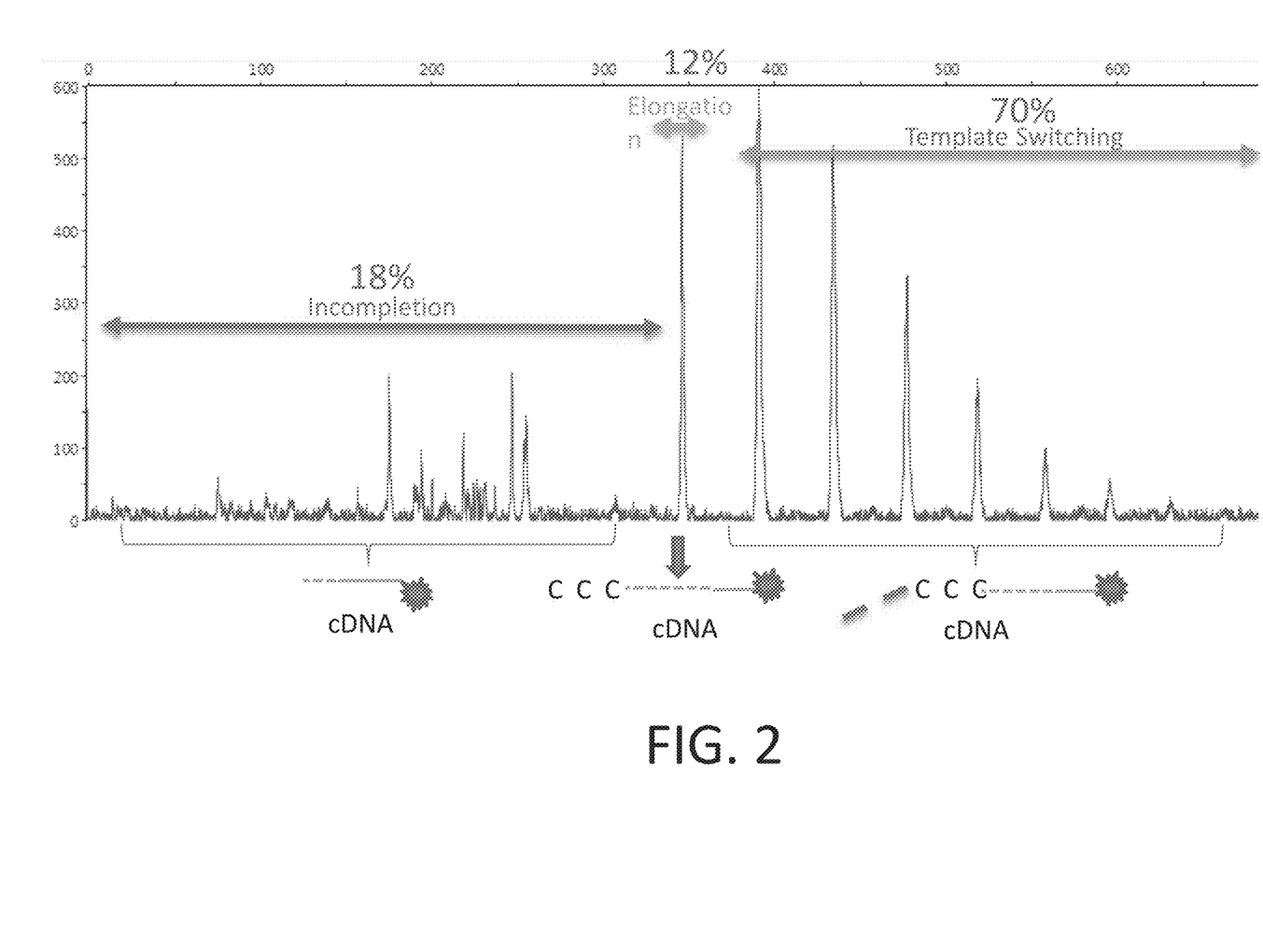
FIG. 2 illustrates how reverse transcription efficiency can be quantified.

A template switching assay was performed. 0.5 µl of 2 µM RNA transcript (200 to 330 nucleotides in length) of varying GC content (from 14% to 88.6%), 0.3 µl of 1 µM FAM primer, 1 µl of 10 mM dNTP, 0.25 µl of RNase Inhibitor, 1 µl of 10 µM template switching oligonucleotide (oligo) and 0.5 µl of reverse transcriptase were combined in a 10 µl reaction volume (using a buffer: 50 mM Tris-HCl, 75 mM KCl, 3 mM MgCl$_2$, pH 8.3). The reaction was incubated at a designated temperature (e.g., 50° C.) for 90 minutes followed by inactivation step at 72° C. for 10 minutes. After the reaction, incomplete products, full length products, and template switched products were quantified by a capillary electrophoresis assay (see Beckman Coulter (Indianapolis, Ind.) "Introduction to Capillary Electrophoresis"). The areas under the peak of incompletion, elongation and template switching products were measured. The transcription efficiency equals to the sum of elongation and template switching divided by the sum of incompletion, elongation and template switching. The relationships between the components used in the assay are shown in FIG. 1. An example of how a capillary electrophoresis chromatogram can be to quantify the incomplete products, full length products, and template switched products is shown in FIG. 2.

Figure 3:
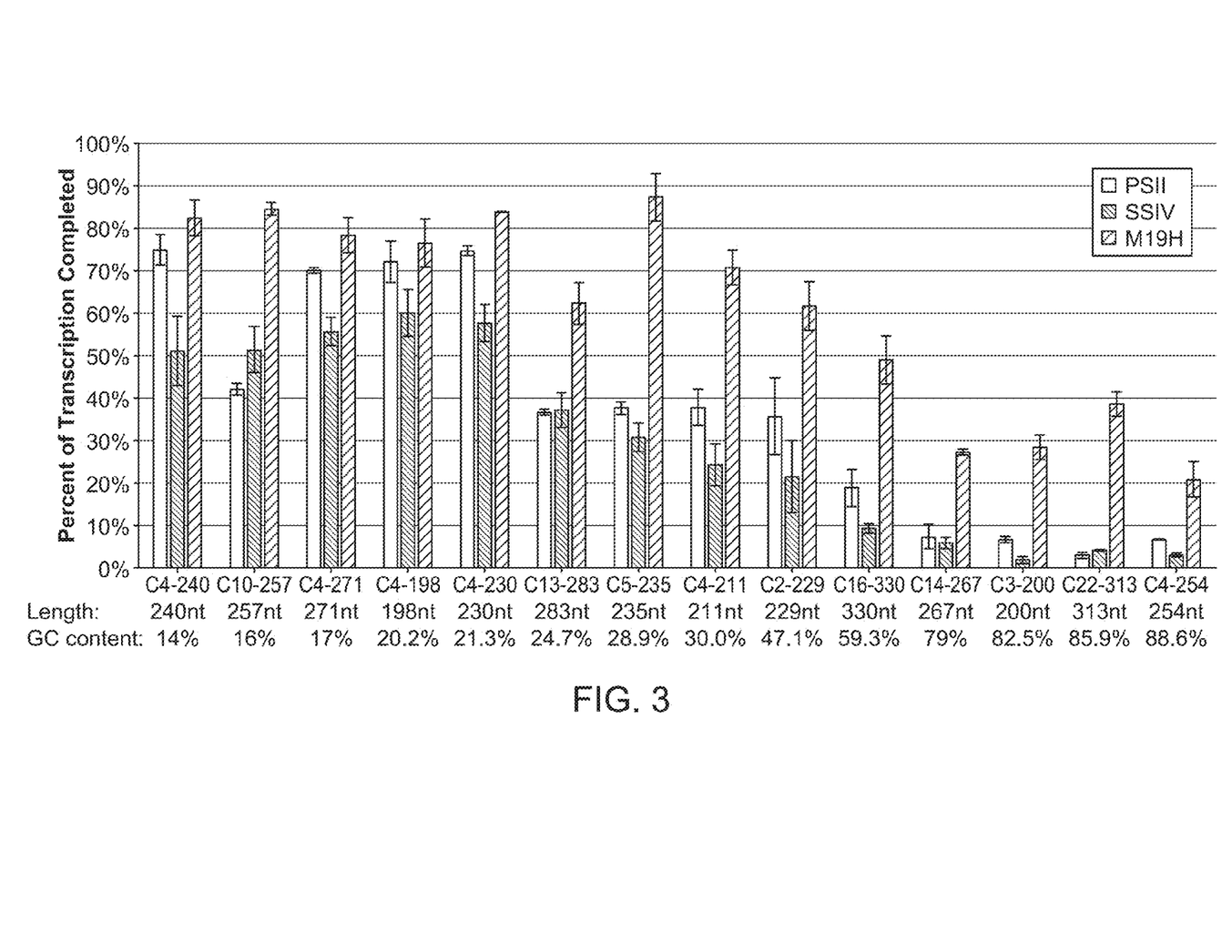
FIG. 3 is a bar chart showing the relative reverse transcription efficiencies of two commercially available MMLV reverse transcriptase variants (SuperScript® IV (Life Technologies, Carlsbad, Calif.) and ProtoScript® II (New England Biolabs, Ipswich, Mass.) and the M19H variant in copying RNA templates with differing GC content.

Based on the results shown in FIG. 3, the M19H enzyme appears to be more efficient than Superscript IV and Protoscript II, particularly for more GC-rich templates, under the conditions used.

What is claimed is:

1. A method comprising:
   (a) obtaining a reaction mix by combining a primer, an RNA template and a reverse transcriptase, wherein the reverse transcriptase comprises: at least 300 contiguous amino acids of SEQ ID NO: 1; and
   (b) incubating the reaction mix to produce cDNA copied from the RNA template.

2. The method of claim 1, wherein the reaction mix is incubated at temperature in the range of 45–60° C.

3. The method of claim 1, further comprises a template switching oligonucleotide.

4. The method of claim 1, wherein the primer is an oligo-dT primer.

5. The method of claim 1, wherein the primer is a random primer.

6. The method of claim 1, wherein the primer is a gene-specific primer.

7. The method of claim 1, wherein the reverse transcriptase comprises an exogenous sequence-specific DNA binding domain.

8. The method of claim 1, wherein the reverse transcriptase comprises an amino acid sequence that is at least 90% identical to at least 300 contiguous amino acids of SEQ ID NO:2 that is C-terminal to the at least 300 contiguous amino acids of SEQ ID NO:1.

9. The method of claim 1, wherein the reverse transcriptase does not have RNAseH activity.

10. The method of claim 1, wherein the reverse transcriptase has RNAseH activity.

11. The method of claim 1, wherein the method comprises: (c) amplifying the cDNA produced in step (b).

12. The method according to claim 11, wherein the amplification is PCR.

13. The method of claim 1, wherein the method comprises quantifying the cDNA produced in step (b).

14. A method comprising:
(a) obtaining a reaction mix by combining a primer, an RNA template and a reverse transcriptase, wherein the reverse transcriptase comprises: (i) amino acids 24-335 of SEQ ID NO: 1 and (ii) an amino acid sequence that is at least 90% identical to amino acids 1-286 of SEQ ID NO: 2 wherein the amino acid sequence of (i) is N-terminal to the amino acid sequence of (ii); and
(b) incubating the reaction mix to produce cDNA copied from the RNA template.

* * * * *